US00RE39600E

(19) United States
(12) Reissued Patent
Devlin, Sr.

(10) Patent Number: US RE39,600 E
(45) Date of Reissued Patent: May 1, 2007

(54) LIQUID SAMPLE DISPENSING METHODS FOR PRECISELY DELIVERING LIQUIDS WITHOUT CROSSOVER

(75) Inventor: William Jackson Devlin, Sr., Lincoln University, PA (US)

(73) Assignee: Dade Behring Inc., Deerfield, IL (US)

(21) Appl. No.: 10/862,911

(22) Filed: Jun. 7, 2004

Related U.S. Patent Documents

Reissue of:
(64) Patent No.: 6,463,969
Issued: Oct. 15, 2002
Appl. No.: 09/829,651
Filed: Apr. 10, 2001

(51) Int. Cl.
*B65B 1/04* (2006.01)

(52) U.S. Cl. ..... 141/130; 422/99; 422/100; 436/43; 436/180; 356/246

(58) Field of Classification Search ..... 141/129, 141/130; 422/99, 100; 73/863.32, 864.91; 436/43, 180; 356/246
See application file for complete search history.

(56) References Cited

U.S. PATENT DOCUMENTS

| | | | |
|---|---|---|---|
| 3,266,322 | A | 8/1966 | Negersmith et al. |
| 4,210,724 | A | 7/1980 | Sogi et al. |
| 4,347,875 | A | 9/1982 | Columbus |
| 4,540,549 | A | 9/1985 | Manabe |
| 4,756,201 | A | 7/1988 | Uffenheimer |
| 4,837,159 | A | 6/1989 | Yamada |
| 4,871,682 | A | 10/1989 | Mazza |
| 5,270,210 | A | 12/1993 | Weyrauch et al. |
| 5,506,142 | A | 4/1996 | Mahaffey et al. |
| 5,536,471 | A | 7/1996 | Clark et al. |
| 5,658,799 | A | 8/1997 | Choperena et al. |
| 5,721,141 | A | 2/1998 | Babson et al. |
| 5,823,744 | A | 10/1998 | Rockwood |
| 6,076,565 | A | 6/2000 | Meyer et al. |
| 6,098,852 | A | 8/2000 | Weiler et al. |

*Primary Examiner*—Steven O. Douglas
(74) *Attorney, Agent, or Firm*—Leland K. Jordan

(57) ABSTRACT

A method for reducing carryover of and delivering liquid taken from a source container by a dispensing means to a target container by spinning the target container so that any liquid within the target container is removed from the dispensing means prior to dispensing liquid into the target container.

21 Claims, 4 Drawing Sheets

LIQUID SAMPLE DISPENSING METHODS FOR PRECISELY DELIVERING LIQUIDS WITHOUT CROSSOVER

Matter enclosed in heavy brackets [ ] appears in the original patent but forms no part of this reissue specification; matter printed in italics indicates the additions made by reissue.

FIELD OF THE INVENTION

The present invention relates to liquid sample dispensing in which a sampling pipette aspirates liquids from a sample or reagent container and dispenses the aspirated liquid into a reaction vessel. More particularly, the invention relates to a system for precisely delivering an amount of liquid from a sample or reagent container into a reaction tube and for reducing carry-over of liquid from one reaction tube to the next, thereby protecting the integrity of the solution within the reaction tube.

BACKGROUND OF THE INVENTION

Various types of tests related to patient diagnosis and therapy can be performed by analysis of a sample of a patient's infections, bodily fluids or abscesses. Such samples are typically placed in sample vials, extracted from the vials, combined with various reagents in special reaction vessels or tubes, incubated, and analyzed to aid in treatment of the patient. Automated clinical analyzers adapted to perform these operations typically handle liquids by aspiration and pressurized dispensing from the sample vials into a reaction vessel using a sampling probe or pipette. In general, a sampling pipette is immersed into a liquid held in a suitable container. A partial vacuum is produced in the pipette in an amount sufficient to draw the required amount of liquid up into the pipette through its nozzle, and the pipette is taken to a station holding a pre-treatment or reaction vessel. At that station, pressure is applied to the interior of the pipette in an amount sufficient to dispense the desired amount of liquid out of the nozzle. The clinical analyzer typically uses a portion or [a liquot] *an aliquot* of the patient's sample that is aspirated from the vial by a sampling pipette. The entire aspirated aliquot or a portion thereby may then be dispensed from the sampling pipette into a reaction vessel or into a sample pre-treatment vessel from which treated sample is later aspirated. Automated clinical analyzers also typically include reagent pipettes adapted to aspirate reagent from reagent containers and to dispense the entire aspirated reagent or a portion thereof into the sample pre-treatment vessel or directly into the reaction vessel.

Conventional pipettes suffer the disadvantage that liquid tends to remain on the exterior surface of the pipette when the pipette is withdrawn after aspiration. In cases of small volumes of aspirated liquid, any excess liquid carried on the exterior of the pipette may be a significant volume with respect to or could even exceed the volume of the aspirated liquid. Pipettes are designed to accurately dispense a predicted volume of liquid; however, any liquid on the exterior surface of the nozzle at the orifice might also be dispensed. Alternatively, the presence of the liquid on the exterior surface might cause the dispensed quantity of liquid to perfuse up the exterior surface, rather than to move into a target vessel. In either case, the volume of liquid received by the vessel is altered in an unpredictable fashion.

Another disadvantage is that reusable probes used to deliver liquid aliquots from successive containers such as tubes or liquid reagent vessels are a source of intra-sample carryover or contamination. Regardless of application, the sampling pipette and reagent pipette must also be thoroughly cleaned and dried between aspirations of different liquids to avoid carryover contamination.

In the prior art are various solutions to the inter-related carryover and contamination problems. To prevent cross-contamination between samples, the pipette may be provided with a removable and disposable "pipette tip" which is the sole portion of the probe to contact the sample liquid. However, disposable pipettes are costly and over a long period of time, become an unexpectedly high item of unwanted expense. Some analyzers include a wiping operation between each aspiration. However, wiping is an extra potential source of contamination, and also introduces additional automated mechanisms that lower the throughput rate and increase the expense of an analyzer.

In order to minimize contamination and carry-over between samples, the probe may be flushed or washed with a diluent liquid such as water. It has also been proposed to utilize a separate probe wash sleeve through which a pressurized rinse liquid is flushed (U.S. Pat. No. 4,756,201). In general, a probe wash chamber is utilized including a wash fluid input into the pipette and a fluid output or exhaust for removing the fluid once the exterior of the pipette has been cleaned. Wash chambers can leak fluid and also can channel along only one side or a portion of the pipette which can leave residue on the pipette exterior. Additionally, if a last drop of wash diluent does not drop off the pipette and is carried back to an aspiration vessel, the droplets dilute the sample or reagent, introducing unwanted sources of error.

Another technique shown, for example in U.S. Pat. No. 3,266,322, aspirates air through the probe by means of a vacuum pump or the aspirating pump used to withdraw the sample liquid from the sample container. Such aspiration, however, introduces the possibility of drawing the unwanted carry-over contaminants deeper into the tubing and apparatus which comprises the sampling system.

U.S. Pat. No. 4,347,875 discloses a "self-cleaning" nozzle for causing liquid remaining behind on the exterior surface of the nozzle to automatically locate itself other than at the aspirating and dispensing orifice. The nozzle comprises a liquid-confining wall extending about a longitudinal axis and terminating in a liquid-dispensing orifice, and an exterior surface having a portion adjacent to the aperture that is adapted to be immersed into a source of the liquid during aspiration. The wall attracts liquid remaining on the adjacent exterior surface after aspiration to loci spaced from the orifice a distance effective to prevent liquid remaining on the exterior surface from interfering with the dispensing of the liquid.

U.S. Pat. No. 4,871,682 discloses an air knife positioned to direct a stream or blast of air across the tip of a sample probe as it is withdrawn from a vessel containing a reagent, diluent, and patient sample solution. After the probe is flushed with diluent, the air knife drives any droplets of diluent fluid off the probe tip into the vessel and thereby prevents contamination or dilution of the sample material in the sample containers.

U.S. Pat. No. 5,506,142 discloses a wash probe in which the simultaneous introduction of pressurized air and water creates a turbulent flow including the use of a pressurized gas stream of short duration to blow the residue of the previous sample out of the probe prior to washing with additional diluent liquid. Also, a waste receptacle is provided which uses a filtered air vent and a liquid saturated material around the probe receiving opening to prevent the escape of aerosols from the receptacle.

[U.S. Pat. No. 5,506,142 provides for a probe wash in which the simultaneous introduction of pressurized air and water creates a turbulent flow including the use of a pressurized gas stream of short duration to blow the residue of the previous sample out of the probe prior to washing with additional diluent liquid. Also, a waste receptacle is provided which uses a filtered air vent and a liquid saturated material around the probe receiving opening to prevent the escape of aerosols from the receptacle.]

U.S. Pat. No. 5,536,471 discloses a bubble flushing syringe for aspirating and dispensing fluids through an open-ended tip. The syringe comprises a piston within a bore formed by a cylindrical wall, wherein the piston forms an annulus with the wall and closed end of the bore, and is capable of reciprocating therein. The syringe further comprises an annular seal seated in the bore and circumventing the piston to retain fluid when the piston reciprocates therethrough. An inlet for directing fluid to the annulus through the wall of the bore and an outlet for directing fluid from the annulus through the wall of the bore to the open-ended tip are positioned proximal to the annular seal and the line generally axially therebetween. A drive device is connected to the piston for reciprocating the piston within the bore. As a result, fluid from the inlet, when connected to a fluid supply, flows around the piston and through the outlet to the open-ended tip, thereby creating a cross-flow pattern in the annulus around the piston as it reciprocates in the bore to flush bubbles through the outlet.

U.S. Pat. No. 5,721,141 discloses a tube washing system including a tube spinning station having a rotatable chuck and a waste chamber surrounding the chuck for capturing and draining tube fluids expelled from a spun tube driven in rotation by the chuck. A pipette for dispensing wash water into a tube is located centrally within the chuck. There is also a tube elevating device located beneath the tube spinning station, the tube elevating device comprising a freely rotatable tube holder, and lift drive motor provided to vertically move the tube holder towards and way from the chuck. The tube used in the washing system has at least one projection provided on its open end which can interlock with a chuck groove.

U.S. Pat. No. 5,827,744 discloses method for cleaning a liquid sample probe in which the probe is positioned within a washing chamber inside a wash body and a purging liquid solution is pumped through the probe into the chamber. A cleaning liquid solution may also be pumped into the chamber around the probe. Either or both liquids are subsequently vacuumed from the chamber drawing air through an annular gap between the probe and the wash body thereby creating a cleaning air flow between the exterior probe surface and the wash body. The cleaning air flow removes all cleaning liquid solution and/or purging liquid solution as the probe is removed from the wash body.

U.S. Pat. No. 6,098,852 discloses a liquid drop dispensing container with a dispensing tip that includes a hollow stem. An interior partition wall within the stem divides the liquid passageway into an upstream chamber and a downstream chamber. The upstream chamber communicates with the interior of the container, and the downstream chamber terminates in a liquid drop outlet. A liquid passage is provided in the interior partition wall and provides flow communication between the upstream chamber and the downstream chamber. A unitary head portion extends into the downstream chamber from the partition wall and defines a rounded liquid impingement surface. Liquid passing from the upstream chamber into the downstream chamber contacts the rounded impingement surface and passes dropwise through the liquid drop outlet.

From this discussion of the art state in automated microbiological analyzers, it may be seen that while there has been considerable effort made toward the problem associated with minimizing contamination and carry-over between samples, there remains an unmet need for a simplified system to address the related problems of precisely delivering an amount of liquid from a sample or reagent container to a reaction tube and for reducing carry-over of liquid from one reaction tube to the next.

SUMMARY OF THE INVENTION

The principal object of the invention is to provide a method for using a sampling pipette that substantially reduces carryover between samples aspirated by the pipette and that is simultaneously adapted to precisely deliver an amount of liquid from a first liquid source container to a first liquid target container. An important aspect of the invention is to provide a sampling pipette in which any liquid within the target container is displaced away from the proximate vicinity of the sampling pipette by axially spinning the target container.

By spinning the target container, liquid therein is moved to inner walls and away from the central portion thereof; consequently, the sampling pipette may be lowered into the target container a sufficient distance to bring a droplet of liquid at the nozzle of the sampling pipette into contact with the bottom of the target container. Physically toughing the droplet with the bottom of the target container releases surface tension energy so that the droplet cleanly flows into the target container without contacting the sampling pipette with any liquid spun against the walls of the target container. Carryover of liquid aspirated and dispensed by the pipette may thereby be minimized between the first source container, the first target container and any subsequently accessed source and target containers.

A further aspect of the invention relates to dispensing a droplet from the sampling pipette in a first step in which a larger portion of the droplet is dispensed into a target container, optionally using the above described method for minimizing carryover of aspirated and dispensed liquids, and the smaller portion is retained within the sampling pipette. After the larger droplet is dispensed, liquid within the target container is displaced away from the proximate vicinity of the sampling pipette by axially spinning the target container, the sampling pipette is lowered into the target container to bring the smaller portion droplet of liquid into contact with the bottom of the target container so that the entire remaining smaller droplet is dispensed. Sensing to confirm the "touching-off" of this smaller droplet assures that the total volume of liquid dispensed in the two steps is bounded at a maximum by the originally aspirated volume and at a minimum by the volume of liquid dispensed in the first step alone.

Briefly summarized, the invention provides a method for reducing carryover of and precisely delivering liquid from a source container to first and subsequent target containers by spinning the target containers so that any liquid within the target container is removed from the dispensing means.

BRIEF DESCRIPTION OF THE DRAWINGS

For more complete understanding of the invention reference is made to the embodiment illustrated in greater detail in the accompanying drawings and the following detailed description.

DETAILED DESCRIPTION OF THE INVENTION

Figure 1:
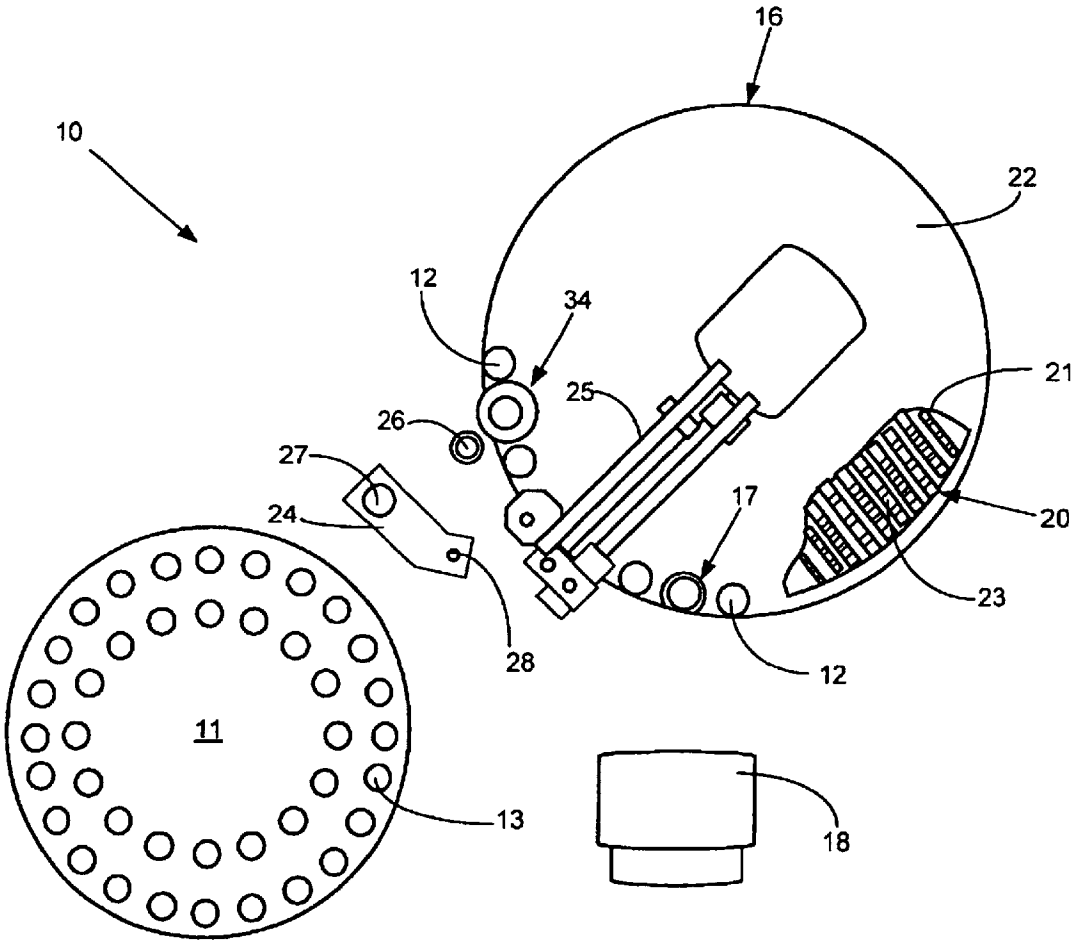
FIG. 1 is a schematic diagram of an automated analyzer in which the present invention may be used to advantage.
Figure 2:
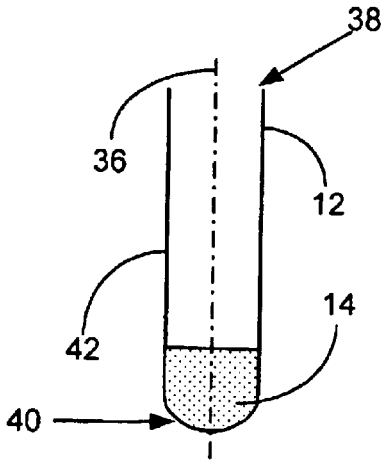
FIGS. 2–6 schematically illustrate the present invention for reducing carryover of liquid from a source container to first and subsequent target containers; and, FIGS. 7–11 schematically illustrate an alternate embodiment of the present invention for delivering liquid from a source container to an empty target container.

The method and apparatus of this invention will be described initially with particular reference to FIG. 1 of the drawings. FIG. 1 shows schematically the elements of a conventional automatic chemical analyzer 10 comprising a sample cup carousel 11 supporting a plurality of open sample tubes 13, a test vessel carousel 14, adapted to hold a plurality of test vessels 12 and to provide plurality of reagent liquid cartridges 20, illustrated as disposed beneath a cut out portion 21 of a lid 22, which covers various thermally controlled compartments. The vessel carousel 14, preferably in the form of a wheel, has about one hundred separate open cavities 17 for holding vessels 12, the inner wall of each cavity having an opening to allow transmission of light. Vessels 12 are seen in FIG. 2 as having a generally cylindrically shape around a central axis 36, also having an open top 38 and a closed bottom 40. Test vessel carousel 14 is provided with means 34 for rotating selected ones of the test vessels 12 around its central axis 36, the rotating means 34 being located proximate selected open cavities 17 holding test vessels 12. Reagent cartridges 20 may be, for example, a multi-compartment container such as those sold under the tradename FLEX® by Dade Behring Inc., Deerfield, Ill., and having a number of different reagents within the multi-compartments 23. A sample liquid arm 24 and a wash resource 26 used to clean a liquid sample aspirating probe 28 described hereinafter are located proximate the sample cup carousel 11 and vessel carousel 14. Sample liquid arm 24 supports sample aspirating probe 28 and is mounted onto a rotatable shaft 27 so that movement of sample liquid arm 24 describes an arc intersecting the sample cup carousel 11, test vessels 12, and wash resource 26. Sample aspirating probe 28 is adapted, for example by cooperation with a peristaltic vacuum pump, to aspirate or withdraw from sample tubes 13 all of or aliquot portions of a patient's specimen and to dispense all of or aliquot portions of a patient's specimen to be tested by analyzer 10.

In a similar manner, a liquid reagent aspirating probe 25 is rotatably mounted above vessel carousel 16 and is adapted to draw reagent liquid from an appropriate compartment 23 of reagent liquid cartridge 20 in cooperation with a peristaltic pump vacuum source and to deposit reagent liquid within a predetermined vessel 12 for processing by the chemical analyzer 10. Probe 25 optionally comprises an ultrasonic mechanism used for aspirating, dispensing and mixing reagents similar to that used in the DIMENSION® chemical analyzer. Photometic analyzing means, not shown, located beneath the vessel carousel 16 measures light absorbence through the vessels 12 at various wavelengths, from which the presence of analyte in the sample liquid may be determined. Photometic analyzing means, not shown, located beneath the vessel carousel 16 measures light absorbence through the vessel 12 at various wavelengths. The photometric analyzing means is of conventional design and includes a photometer and a source lamp that emits a light beam which passes through various lens housed in a rotatable detector arm to a photodetector which, being mounted on the outer-end of the detector arm adjacent the outer periphery of the vessels 12, rotates about the vessel carousel 16. The photodetector relays absorbence readings through the computer where the readings are converted into concentration units. A conventional computer 18 using a microprocessor is used to control the various components of the analyzer 10 and to store system parameter changes and test results. The chemical analyzer 10 may be, for example, the DIMENSION® clinical analyzer sold by Dade Behring Inc., Deerfield, Ill., or another similar analyzer commercially available to clinical laboratories.

The present invention adds to analyzer 10 or similar analyzers available to clinical laboratories a method to precisely deliver an amount of liquid from a first sample tube 13 into a test vessel 12 and for reducing carryover of liquid within a first test vessel 12 tube to either a second test vessel 12 or to a second sample tube 13, thereby protecting the integrity of the solution within test vessels 12 and sample tubes 13. In a more general sense, the present invention provides an method for reducing carryover of and precisely delivering liquid from a source container to a target container by spinning the target container so that any liquid within the target container is removed from the vicinity of the dispensing means. For the purpose of describing the invention, reference will be made to the aforedescribed sample tube 13 as a source container and test vessel 12 as a target container.

Figure 3:
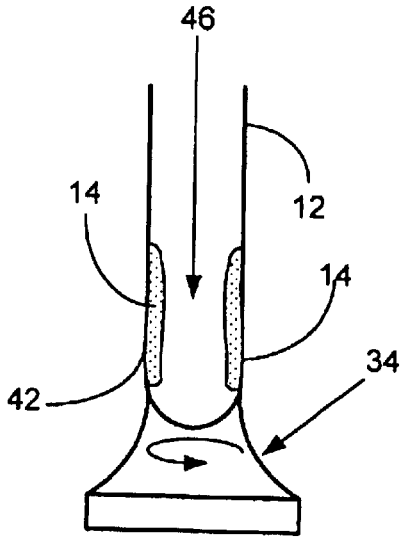
Figure 4:
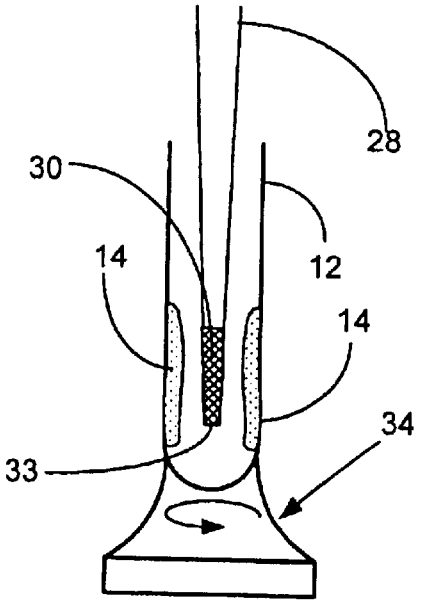

FIG. 2 illustrates a test vessel 12 as a target container having an amount of liquid 14 previously disposed therein, for example an amount of reagent taken from a compartment 23 and dispensed therein by liquid reagent aspirating probe 25. Test vessel 12 is shown as being generally symmetrical around axis 36 for purposes of illustration only. In practicing the present invention, a target container need not be symmetrical as long as it may be rotated around a central axis as described next. Prior to the introduction into target test vessel 12 of additional liquid taken from a source container sample tube 13 by sample aspirating probe 28, target test vessel 12 is caused to rotate around axis 36 by a source 34 of rotational motion. Rotational source 34 may comprise a motor shaft with a tube clamp 25 mounted thereon, a friction belt driven by a motor, or other similar mechanisms for rotating target test vessel 12 around axis 36 at a speed sufficient to cause liquid 14 disposed therein to move upwards from the bottom 40 of target test vessel 12 along the inner walls 42 and away from the central portion 46 thereof, as illustrated in FIG. 3. By spinning the target container 12, liquid therein is removed from the path of a sample aspirating probe 28, as illustrated in FIG. 4, containing an amount of sample liquid 30 aspirated therein. In the present invention, sample aspirating probe 28 may have either of a permanent type or of a disposable type aspirating probe design.

Figure 5:
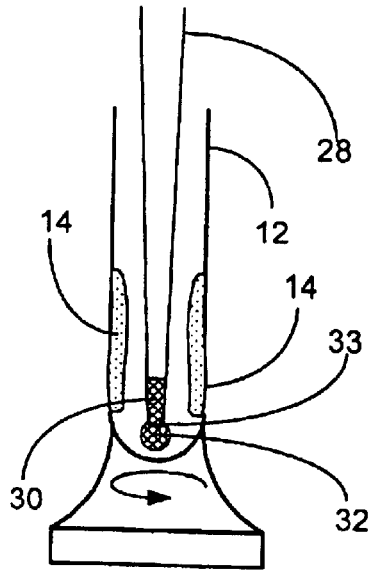
Figure 6:
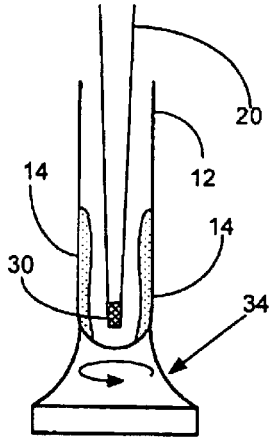

As a result of liquid within the target container 12 being removed from the path of sample aspirating probe 28, aspirating probe 28 may be inserted and lowered into the target container 12 a sufficient distance to bring a droplet of source liquid 32 formed at the nozzle of the aspirating probe 28 using, for example a peristaltic vacuum pump (not shown), into contact with the bottom 40 of the target container 12, as illustrated in FIG. 5 without the sampling pipette or the droplet touching any of the liquid 14 previously disposed therein. Physically toughing the droplet 32 with the bottom 40 of the target container 12 releases surface tension energy so that the droplet 32 cleanly flows into the target container 12 and not allowing any physical contact between the aspirating probe 28 and any liquid spun against the walls 42 of the target container 12, as seen in FIG. 6. In FIG. 6, the previous droplet of liquid 32 formed at the nozzle 33 of aspirating probe 28 has also spun against the walls 42 of the target container 12 and admixed with liquid 14 maintained along the inner walls 42 of the target container 12 by the centrifugal forces generated by rotational motion of the target container 12. This embodiment of the present invention is thus seen to provide a simple method for eliminating contamination of the aspirating probe 28 dispensing means by spinning the target container 12 so that any liquid within the target container 12 is removed away from the dispensing means when liquid from the source container sample tube 15 is dispensed therein by the aspirating probe 28. After this dispensing of the initial droplet of liquid 32 into the target container 12 by aspirating probe 28 without touching any of the liquid 14 previously disposed therein, the sample liquid remaining within aspirating probe 28 may similarly be dispensed into subsequent target containers 12 without the aspirating probe 28 touching any liquids disposed therein. This may be accomplished by axially spinning a subsequent target vessel so that target vessel liquid contained therein is displaced away from the central portion of the target vessel; forming another droplet of source liquid at the nozzle of the sampling pipette and lowering the sampling pipette into the central portion of the subsequent target vessel a distance sufficient to cause the second droplet of source liquid to contact the bottom of the subsequent target vessel without the sampling pipette or the droplet touching second target vessel liquid disposed therein. Prior to the aspirating probe 28 being used to aspirate any additional source liquids taken from another source container sample tube 13, the aspirating probe 28 is typically cleaned by insertion into a conventional wash resource 26. This embodiment of the present invention is thereby seen to provide a simple method for eliminating carryover of liquid aspirated and dispensed by the aspirating probe 28 between the source container sample tube 13, the first target test vessel 12 and any subsequently accessed target containers 12.

Figure 7:
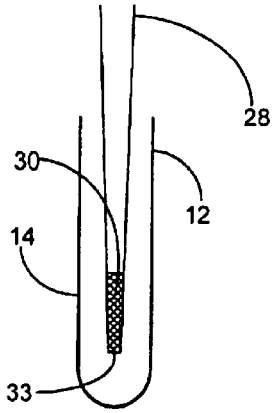
Figure 8:
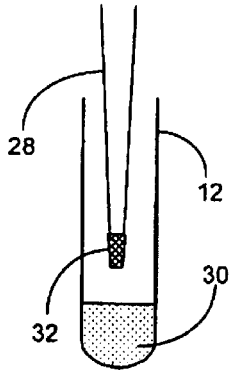

In an alternate embodiment, the present invention may also be useful in overcoming uncertainties associated with dispensing of a known volume of aspirated liquid that arise due to any portion of the aspirated liquid remaining behind on the exterior surface of the nozzle. This embodiment is illustrated in FIG. 7 in which a known volume of liquid 30 is shown as aspirated into aspirating probe 28 using, for example a precisely metered peristaltic vacuum pump (not shown), and the aspirating probe 28 has been inserted a distance above the bottom 40 of an empty and stationary target vessel 12. The peristaltic vacuum pump is operated to dispense a major portion, for example about 98%, of the known volume of liquid 30 into the stationary target vessel 12., as shown in FIG. 8, leaving a minor droplet portion 32, in this example about 2% of liquid 30 within the nozzle 33 of the aspirating probe 28. The peristaltic vacuum pump is operated so that the size of the minor portion is sufficiently small to ensure that surface tension forces within the droplet 32 will retain the droplet 32 at the nozzle 33 of the aspirating probe 28.

Figure 9:
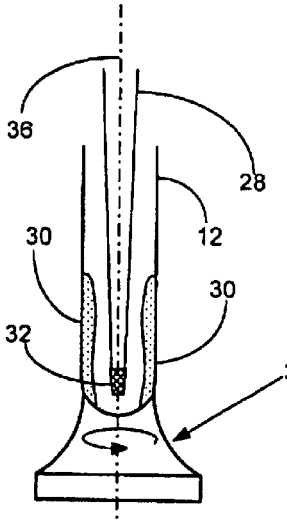
Figure 10:
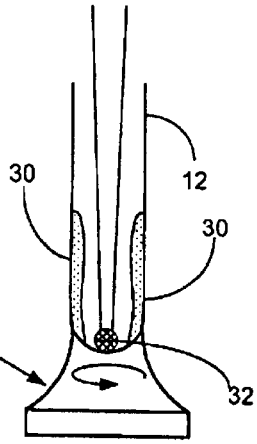
Figure 11:
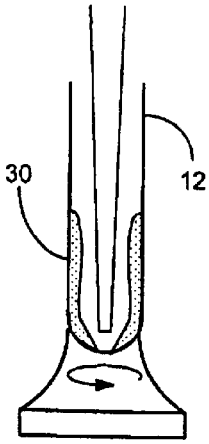

As described before, target test vessel 12 is next caused to rotate around axis 36 by a source 34 of rotational motion at a speed sufficient to cause liquid 30 dispensed therein to move upwards from the bottom 40 of target test vessel 12 along the inner walls 42 and away from the central portion 46 thereof, as illustrated in FIG. 9. After the dispensed major portion of liquid 30 into the target container 12 is moved upwards from the bottom 40 to the inner walls 42 by centrifugal forces generated by the rotational motion of the target test vessel 12, aspirating probe 28 may be lowered into the target vessel 12 to bring minor droplet portion 32 at the nozzle of the aspirating probe 28 into contact with the bottom 40 of the rotating target container 12, as illustrated in FIG. 10, thereby releasing surface tension energy so that the droplet 32 cleanly flows into the target vessel minimizing the amount of any aspirated liquid remaining behind on the exterior surface of the nozzle. The minor droplet portion 32 then admixes with the major portion of liquid 30 along the inner walls 42 of the target vessel 12, illustrated in FIG. 11.

In this embodiment, the present invention ensures that the total amount of liquid 30 dispensed into the target vessel 12 is less than the total volume of liquid 30 originally aspirated into aspirating probe 28 and, at the same time, is greater than the major portion of the known volume of liquid 30. It should be noted by the reader that while this alternate embodiment may be practiced when the target vessel 12 is originally empty, as described above, in an instance that the target vessel 12 originally contains a liquid 14, like shown in FIG. 2, then as described in conjunction with FIGS. 3 and 4, the target test vessel 12 may be rotated to cause liquid 14 disposed therein to move from the bottom 40 of target test vessel 12 along the inner walls 42 and away from the central portion 46 thereof, as illustrated in FIG. 3 and away from the path of the sample aspirating probe 28, as illustrated in FIG. 4.

Figure 12:
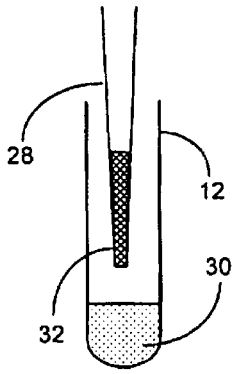
FIGS. 12–17 schematically illustrate an embodiment of the present invention for delivering liquid from a source container to a target container already containing liquid.
Figure 13:
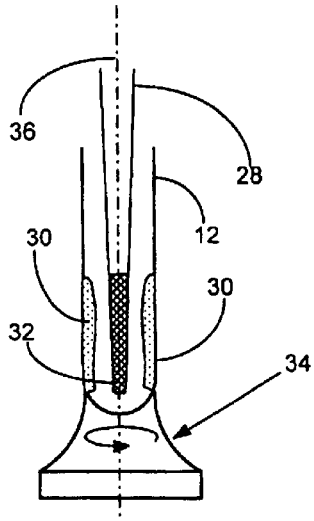

Such an embodiment is illustrated in FIGS. 12–17 where, beginning with FIG. 12, a target vessel 12 contains target fluid 30 therein a and a known amount of source liquid 32 has been aspirated from a source vessel into an aspirating probe 28. The target vessel is spun around its axis 36, FIG. 13, so that the target liquid 30 contained therein is displaced away from the central portion 46 and the bottom portion 40 (see FIGS. 2 and 3) of the target vessel 12.

Figure 14:
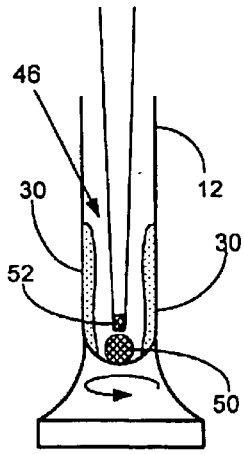
Figure 15:
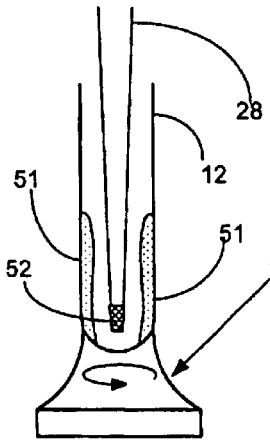

Next, the sampling pipette 28 is lowered into the central portion 46 of the target vessel 12 a distance sufficient to cause a major portion 50 of the volume of source liquid 32 to contact the bottom of the target vessel 12, FIG. 14, without the major portion 12 touching target liquid 30 disposed therein, so that the major portion 50 of source liquid 32 is spun off from the sampling pipette 28 into the target vessel 12. The target vessel 12 continues to spin so that the target liquid 30 and the major portion 50 of source liquid 32 contained therein are displaced away from the central portion of the target vessel, FIG. 15, and admixed together, illustrated as mixture 51.

Figure 16:
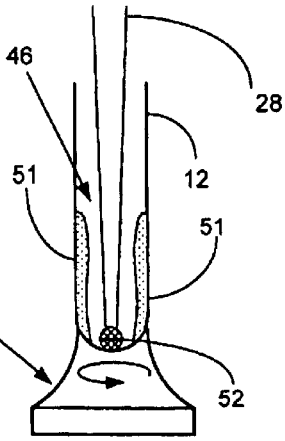
Figure 17:
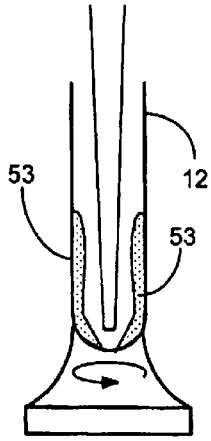

Subsequently, a minor droplet 52 of the remaining portion of source liquid 32 is formed at the nozzle of the sampling pipette 28 and the sampling pipette 28 is again lowered into the central portion 46 of the target vessel 12 a distance sufficient to cause the remaining minor droplet portion 52 of source liquid 32 to contact the bottom of the target vessel 12 without the remaining minor droplet portion 52 touching liquid mixture 51 disposed therein, FIG. 16, so that the remaining minor droplet portion 52 of source liquid is spun off from the sampling pipette into the target vessel 12, FIG. 17, and admixed together with mixture 51, illustrated as mixture 53.

It is to be understood that the embodiments of the invention disclosed herein are illustrative of the principles of the invention and that other modifications may be employed which are still within the scope of the invention. For example, if small amounts of liquid are involved, rather than spinning the target vessel to remove liquid therein from the path of the aspirating probe, the target vessel may be inclined at an angle to remove liquid from the bottom portion of the target vessel so that the aspirating probe may be lowered into the target container to bring the droplet of liquid at the nozzle of the aspirating probe into contact with the bottom of the target container without touching any of the liquid previously disposed therein. Accordingly, the present invention is not limited to those embodiments precisely shown and described in the specification but only by the following claims.

What is claimed is:

1. A method for reducing carryover of the first target vessel liquid contained in a first target vessel and a sampling pipette containing source liquid, the method comprising:

spinning the first target vessel so that the first target vessel liquid contained therein is displaced away from the central portion of the target vessel;

forming a first droplet of source liquid at the nozzle of the sampling pipette;

lowering the sampling pipette into the central portion of the target vessel a distance sufficient to cause the first droplet of source liquid to contact the bottom of the first target vessel [without the sampling pipette or the droplet touching first target vessel liquid disposed therein,] so that the first droplet of source liquid is spun off from the sampling pipette into the target vessel.

2. The method of claim 1 further comprising:

spinning a second target vessel so that second target vessel liquid contained therein is displaced away from the central portion of the second target vessel;

forming a second droplet of source liquid at the nozzle of the sampling pipette;

lowering the sampling pipette into the central portion of the second target vessel a distance sufficient to cause the second droplet of source liquid to contact the bottom of the second target vessel [without the sampling pipette or the droplet touching second target vessel liquid disposed therein,] so that the second droplet of source liquid is spun off from the sampling pipette into the second target vessel.

3. The method of claim 1 wherein the target vessel is axially [symetrical] *symmetrical*.

4. The method of claim 1 wherein the sampling pipette is either a permanent or disposable sampling pipette.

5. A method for reducing carryover of first target vessel liquid contained in a first target vessel and a sampling pipette containing source liquid, the method comprising:

inclining the first target vessel so that first target vessel liquid contained therein is displaced away from the central portion of the target vessel;

forming a first droplet of source liquid at the nozzle of the sampling pipette;

lowering the sampling pipette into the central portion of the target vessel a distance sufficient to cause the first droplet of source liquid to contact the bottom of the first target vessel [without the sampling pipette or the droplet touching first target vessel liquid disposed therein,] so that the first droplet of source liquid is spun off from the sampling pipette into the target vessel.

6. The method of claim 5 further comprising:

inclining a second target vessel so that second target vessel liquid contained therein is displaced away from the central portion of the second target vessel;

forming a second droplet of source liquid at the nozzle of the sampling pipette;

lowering the sampling pipette into the central portion of the second target vessel a distance sufficient to cause the second droplet of source liquid to contact the bottom of the second target vessel [without the sampling pipette or the droplet touching second target vessel liquid disposed therein,] so that the second droplet of source liquid is spun from the sampling pipette into the target vessel.

7. The method of claim 5 wherein the target vessel is axially [symetrical] *symmetrical*.

8. The method of claim 5 wherein the sampling pipette is either a permanent or disposable sampling pipette.

9. A method for delivering an amount of liquid from a source vessel into a target vessel, the method comprising:

aspirating a known volume of liquid from the source container into an aspirating probe;

dispensing a major portion of the volume of liquid into the target vessel while the target vessel is stationary, at the same time leaving a minor portion of liquid within the aspirating probe;

spinning the target vessel so that the major portion of liquid contained therein is displaced away from the central portion of the target vessel;

forming a droplet of the minor portion of source liquid at the nozzle of the sampling pipette;

lowering the sampling pipette into the central portion of the target vessel a distance sufficient to cause the droplet of source liquid to contact the bottom of the target vessel [without the droplet touching liquid disposed therein,] so that the droplet of source liquid is spun off from the sampling pipette into the target vessel.

10. The method of claim 9 wherein the target vessel is axially [symetrical] *symmetrical*.

11. The method of claim 9 wherein the sampling pipette is either a permanent or disposable sampling pipette.

12. A method for delivering an amount of source liquid from a source vessel into a target vessel containing target liquid therein, the method comprising:

aspirating a known volume of source liquid from the source container into an aspirating probe;

spinning the target vessel so that target liquid contained therein is displaced away from the central portion of the target vessel;

lowering the sampling pipette into the central portion of the target vessel a distance sufficient to cause a major portion of the volume of source liquid to contact the bottom of the target vessel [without the major portion touching target liquid disposed therein,] so that the major portion of source liquid is spun off from the sampling pipette into the target vessel;

continuing to spin the target vessel so that all liquid contained therein is displaced away from the central portion of the target vessel;

forming a droplet of the remaining droplet portion of source liquid at the nozzle of the sampling pipette;

lowering the sampling pipette into the central portion of the target vessel a distance sufficient to cause the remaining droplet portion of source liquid to contact the bottom of the target vessel [without the remaining droplet portion touching liquid disposed therein,] so that the remaining droplet portion of source liquid is spun off from the sampling pipette into the target vessel.

13. The method of claim 12 wherein the target vessel is axially symmetrical.

14. The method of claim 13 wherein the sampling pipette is either a permanent or disposable sampling pipette.

*15. The method of claim 1, wherein the sampling pipette is lowered into the central portion of the target vessel without the sampling pipette or the droplet touching first target vessel liquid disposed therein.*

*16. The method of claim 2, wherein the sampling pipette is lowered into the central portion of the target vessel without the sampling pipette or the droplet touching second target vessel liquid disposed therein.*

*17. The method of claim 5, wherein the sampling pipette is lowered into the central portion of the target vessel without the sampling pipette or the droplet touching first target vessel liquid disposed therein.*

*18. The method of claim 6, wherein the sampling pipette is lowered into the central portion of the target vessel without the sampling pipette or the droplet touching second target vessel liquid disposed therein.*

*19. The method of claim 9, wherein the sampling pipette is lowered into the central portion of the target vessel without the droplet touching liquid disposed therein.*

*20. The method of claim 12, wherein the sampling pipette is lowered into the central portion of the target vessel a distance sufficient to cause a major portion of the volume of source liquid to contact the bottom of the target vessel without the major portion touching target liquid disposed therein.*

*21. The method of claim 12, wherein the sampling pipette is lowered into the central portion of the target vessel a distance sufficient to cause the remaining droplet portion of source liquid to contact the bottom of the target vessel without the remaining droplet portion touching liquid disposed therein.*

* * * * *